United States Patent [19]

Mörsdorf et al.

[11] Patent Number: 4,948,802

[45] Date of Patent: Aug. 14, 1990

[54] GUANIDINE CARBOXYLIC ACID ESTERS AND PHARMACEUTICAL PREPARATIONS CONTAINING THESE COMPOUNDS

[75] Inventors: Peter Mörsdorf, Langenzenn; Helmut Schickaneder, Eckental; Volker Pfahlert, Nuremberg; Heidrun Engler, Cadolzburg; Armin Buschauer; Walter Schunack, both of Berlin, all of Fed. Rep. of Germany

[73] Assignee: Heumann Pharma GmbH & Co., Nuremberg, Fed. Rep. of Germany

[21] Appl. No.: 180,135

[22] Filed: Apr. 11, 1988

[30] Foreign Application Priority Data

Aug. 7, 1987 [DE] Fed. Rep. of Germany ....... 3726381

[51] Int. Cl.$^5$ .................. A61K 31/445; C07D 401/12
[52] U.S. Cl. ..................................... 514/341; 546/278; 548/336; 548/342; 548/196; 544/331; 514/397; 514/400; 514/371; 514/275
[58] Field of Search .......................... 546/278; 514/341

[56] References Cited

U.S. PATENT DOCUMENTS 3,881,015  4/1975  Black et al. .................... 514/400
3,968,216  7/1976  Black et al. .................... 514/357

FOREIGN PATENT DOCUMENTS 2053175   7/1971  Fed. Rep. of Germany .
2630847   1/1978  Fed. Rep. of Germany .
3512084  10/1986  Fed. Rep. of Germany .
3528214   2/1987  Fed. Rep. of Germany .
3528215   2/1987  Fed. Rep. of Germany .
1305547   2/1973  United Kingdom .

OTHER PUBLICATIONS

Chem. Abstracts 103:153321a, Durant et al.

Primary Examiner—Jane T. Fan
Attorney, Agent, or Firm—Burns, Doane, Swecker & Mathis

[57] ABSTRACT

New guanidine carboxylic acid esters corresponding to the general formula I

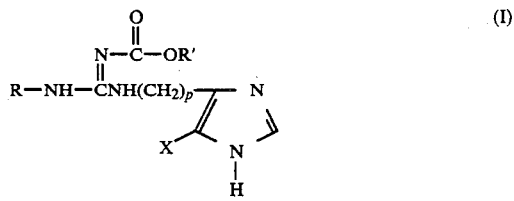

and a process for the preparation of these compounds are described. The compounds according to the invention are $H_2$-agonists optionally having an additional $H_1$-antagonistic component. They are distinguished by their improved oral activity. The use of the above-mentioned guanidine carboxylic acid esters and of pharmaceutical preparations containing these esters is also described.

15 Claims, No Drawings

GUANIDINE CARBOXYLIC ACID ESTERS AND PHARMACEUTICAL PREPARATIONS CONTAINING THESE COMPOUNDS

DESCRIPTION

Histamine-$H_2$-agonists such as, for example, impromidine (G. J. Durant et al., Nature (London) 1978, 276, 403) produce a marked increase in contractility by stimulation of the $H_2$ receptors of the heart in vivo and on the basis of their positive inotropic action they have been proposed for the treatment of cardiac insufficiency and in particular congestive cardiomyopathy.

DE-OS 3 512 084, 3 528 214 and 3 528 215 and EP-OS 0 199 845 have described new $H_2$ agonists in which undesirable side effects of impromidine could be eliminated by the incorporation of additional $H_1$-antagonistic units but at the same time the activity of the compounds could be considerably increased. These compounds show excellent effects when applied parenterally but are considerably less active when administered orally.

It is therefore an object of the present invention to provide $H_2$-agonists which may contain additional $H_1$-antagonistic components and are distinguished by their improved activity when administered orally.

This problem is solved by the present invention.

The invention relates to quanidine carboxylic acid esters corresponding to the general formula I

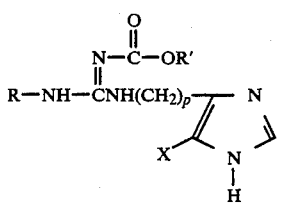

wherein (a) R denotes a group of the formula

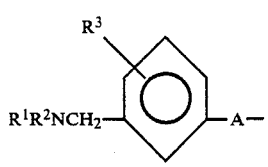

wherein $R^1$ and $R^2$, which may be identical or different, stand each for hydrogen, a straight chained $C_1$-$C_6$-alkyl group or a $C_5$-$C_6$-cycloalkyl group or $R^1$ and $R^2$ together with the nitrogen atom to which they are attached form a 5- to 10-membered nitrogen-containing alicyclic, heterocyclic ring, $R^3$ stands for a hydrogen atom, a halogen atom or a $C_1$-$C_3$-alkoxy group, and A denotes a group of the formula —O—$(CH_2)_k$—, —O—$CH_2CH(OH)CH_2$—, —O—$CH_2CH(CH_3)$—$CH_2$—, —$CH_2$—O—$CH_2$—CH(OH)—$CH_2$— or —O—$CH_2$—CH(OH)—CH(OH)—$CH_2$, wherein k has the value 3 or 4, or (b) R denotes a group of the formula

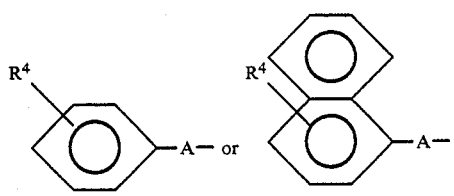

wherein $R^4$ stands for a hydrogen atom, a halogen atom preferably attached in the para-position to A, a $C_1$-$C_3$-alkoxy group or a $C_1$-$C_3$-alkyl group and A has the meanings mentioned under (a), or (c) R denotes a group of the formula

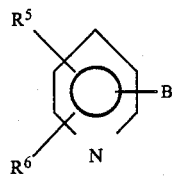

wherein $R^5$ and $R^6$, which may be identical or different, stand each for a hydrogen atom, a halogen atom, a straight chained $C_1$-$C_3$-alkyl group or a straight chained $C_1$-$C_3$-alkoxy group, B may be attached in the 2-, 3- or 4-position of the pyridine ring and denotes a group of the formula

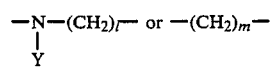

wherein 1 has the value 2, 3 or 4 and m has the value 3, 4 or 5 and Y stands for a hydrogen atom or a straight chained $C_1$-$C_3$-alkyl group or (d) R denotes a group of the formula

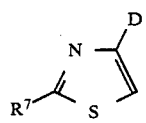

wherein $R^7$ stands for a group of the formula $(R^1R^2)N$—$CH_2$—, $(H_2N)_2C$=N—,

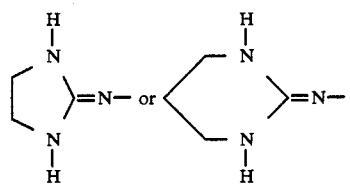

wherein $R^1$ and $R^2$ have the meanings indicated under (a), D stands for a group of the formula —$CH_2$—S—$(CH_2)_n$— or —$(CH_2)_o$— wherein n has the value 2 or 3 and o has the value 2, 3 or 4, or (e) R denotes a group of the formula

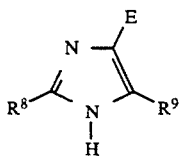

wherein $R^8$ stands for a hydrogen atom, a benzyl group optionally substituted by a halogen atom, a group of the formula $(R^1R^2)N—CH_2—$ or an amino group, $R^1$ and $R^2$ have the meanings mentioned under (a), $R^9$ denotes a hydrogen atom or a straight chained $C_1$-$C_3$-alkyl group or $C_1$-$C_3$-alkylthio group, E stands for a group of the formula $—CH_2—S—(CH_2)_n—$

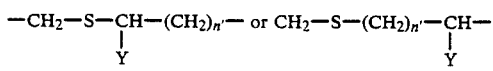

wherein n has the value 2 or 3, n' has the value 1, 2 or 3 and Y has the meanings indicated above under (c), or (f) R denotes a group of the formula

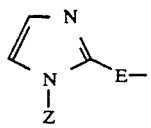

wherein Z denotes a hydrogen atom or a straight chained $C_1$-$C_3$-alkyl group and E has the meanings indicated above under (e) or (g) R denotes a group of the formula $R''—A'—B'—$ wherein $R''$ stands for a substituted or unsubstituted phenyl group or a substituted or unsubstituted naphthyl group, $A'$ stands for a single bond or for a group of the formula $—CR^{1'}R^{2'}$ or for a nitrogen atom substituted with an optionally substituted aryl, hetaryl or benzyl group or with a straight chained $C_1$-$C_3$-alkyl group, $R^{1'}$ denoting a hydrogen atom or a methyl group and $R^{2'}$ denoting an optionally substituted phenyl group or an optionally substituted hetaryl group, and $B'$ stands for a group of the formula $—CH(Y)—S—(CH_2)_{m'}—$, $—CH_2—S—CH_2—CH(Y)—CH_2—$, $—CH_2—S—CH(Y)—CH_2—$, $—CH_2—S—(CH_2—CH(Y)—$, $—(CH_2)_{n''}—$, $—CH_2—CH(Y)—$, $—(CH_2)_{n''}—CH(Y)—$, $—O—(CH_2)_2—$, $—CH_2—O—(CH_2)_{o'}—$, $—CH_2—O—CH_2—CH(Y)—CH_2—$, $—O—CH_2—CH(Y)—$, $—O—CH(Y)—CH_2—$, $—S—(CH_2)_q—$, $—S—CH_2—CH(Y)—$, $—S—CH(Y)—CH_2—$ or $—S—CH_2—CH(Y)—CH_2$, wherein Y denotes a hydrogen atom or a straight chained $C_1$-$C_3$-alkyl group, $m'$ and $o'$ have each the value 2 or 3 and $n''$ and q have each the value 2, 3, 4 or 5, or (h) R denotes a group of the formula $R'''—A''—B''$ wherein $R'''$ stands for a substituted or an unsubstituted hetaryl group on which a phenyl ring may be condensed, $A''$ stands for a single bond or for a group of the formula $—CR^{1'}R^{2'}—$ or for a nitrogen atom substituted with an optionally substituted aryl, hetaryl or benzyl or a straight chained $C_1$-$C_3$-alkyl group, $R^{1'}$ denoting a hydrogen atom or a methyl group and $R^{2'}$ denoting an optionally substituted phenyl group or an optionally substituted hetaryl group, and $B''$ stands for a group of the formula $—CH(Y)—S—(CH_2)_{m'}—$, $—CH_2—S—CH_2—CH(Y)—CH_2—$, $—CH_2—S—CH(Y)—CH_2—$, $—(CH_2)_{n''}—CH(Y)—$, $—CH_2—S—CH_2—CH(Y)—$, $—(CH_2)_{n''}—$, $—O(CH_2)_{n''}—$, $—S—CH_2—CH(Y)—$, $S—CH(Y)—CH_2—$, $—S—(CH_2)_q—$ or $—S—CH_2—CH(Y)—CH_2—$, wherein Y denotes a hydrogen atom or a straight chained $C_1$-$C_3$-alkyl group, $m'$ has the value 2 or 3 and $n''$ and q have each the value 2, 3, 4 or 5, and $R'$ denotes a straight chained or branched $C_1$-$C_6$-alkyl or cycloalkyl group optionally substituted once or more than once with a halogen atom, a $C_1$-$C_3$-alkoxy group and/or an aryl group or it denotes an unsubstituted or a mono-or multi-substituted phenyl ring, p has the value 2 or 3 and X denotes a hydrogen atom or a methyl group, and the physiologically acceptable salts thereof.

In the general formula I, the substituent R has various meanings according to the embodiments (a) to (h) of the present invention.

In all the embodiments, $R'$ stands for a straight chained or branched $C_1$-$C_6$-alkyl group, preferably a $C_1$-$C_4$-alkyl group, optionally substituted once or more than once with a halogen atom, a $C_1$-$C_3$-alkoxy group and/or an aryl group. When $R'$ is substituted, it is preferably mono- to tri-substituted with a halogen atom, e.g. a chlorine, bromine or iodine atom, a $C_1$-$C_3$-alkoxy group and/or an aryl group, in particular a phenyl group. An unsubstituted $C_1$-$C_4$-alkyl group is particularly preferred, e.g. the methyl, ethyl, n-propyl, isopropyl, n-butyl or sec.-butyl group. Further, $R'$ may denote a cycloalkyl group, preferably a $C_5$-$C_6$-cycloalkyl group, or an optionally substituted phenyl ring. If the phenyl ring is substituted, it may be substituted with one or more, preferably 1 to 3 substituents selected from halogens such as chlorine, bromine or iodine, $C_1$-$C_3$-alkyl and $C_1$-$C_3$-alkoxy. X denotes a hydrogen or a methyl group and p has the value 2 or 3, preferably the value 3.

In embodiment (a), R denotes a group of the formula

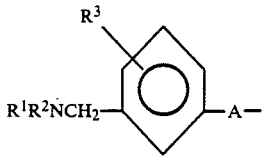

wherein $R^1$ and $R^2$, which may be identical or different, each denote a hydrogen atom, a straight chained $C_1$-$C_6$-alkyl group, preferably a straight chained $C_1$-$C_3$-alkyl group such as, for example, a methyl, ethyl or n-propyl group, in particular a methyl group, or a $C_5$-$C_6$-cycloalkyl, but $R^1$ and $R^2$ together with the nitrogen atom to which they are attached may also form a 5- to 10-membered nitrogen-containing heterocyclic ring. Preferred examples of the 5- to 10-membered heterocyclic ring defined above are the pyrrolidine, piperidine and homopiperidine ring. $R^3$ stands for a hydrogen atom or a halogen atom, for example a chlorine, bromine or iodine atom, which is attached in the ortho-, meta- or para-position to the $(R^1R^2)NCH_2$, preferably in the ortho-position to the said group. $R^3$ may, furthermore, denote a $C_1$-$C_3$-alkoxy group, e.g. a methoxy, ethoxy or propoxy group, preferably a methoxy group, and this group is also attached in the ortho-, meta- or para-position, preferably in the para-position to the $(R^1R^2)NCH_2$ group. A denotes one of the following groups: $—O(CH_2)_k—$, $—O—CH_2CH(OH)CH_2—$, $—O—CH_2—CH(CH_3)—CH_2—$, $—CH_2—O—CH_2CH(OH—$ )—CH₂— or —O—CH₂—CH(OH)—CH(OH)—CH₂—. In the above formula, k has the value 3 or 4, 3 being preferred.

In embodiment (b), R denotes a group of the formula

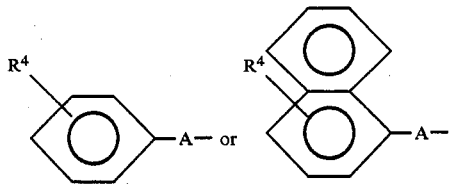

wherein $R^4$ stands for a hydrogen atom, a halogen atom which is preferably attached in the para-position to A, e.g. a chlorine, bromine or iodine atom, preferably a chlorine atom, a $C_1$-$C_3$-alkoxy group, for example a methoxy or ethoxy group, a $C_1$-$C_3$-alkyl group, for example a methyl or ethyl group, or most preferably a hydrogen atom. The symbol A has the meaning defined in the description of embodiment (a), the group —O—(CH₂)₃— or —O—CH₂CH(OH)CH₂— being preferred.

In embodiment (c), R denotes a group of the formula

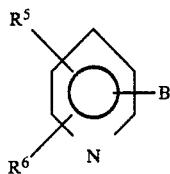

wherein $R^5$ and $R^6$, which may be identical or different, denote each a hydrogen atom or a halogen atom, e.g. a fluorine, chlorine or bromine atom, preferably a bromine atom. The halogen atom or atoms is or are preferably attached in the 3- and/or 5-position of the pyridine ring. When $R^6$ is a hydrogen atom then $R^5$ is preferably a halogen atom, for example a fluorine, chlorine or bromine atom, especially a bromine atom. $R^5$ and $R^6$ may also each stand for a $C_1$-$C_3$-alkyl group or a $C_1$-$C_3$-alkoxy group as defined above under (a). This group or these groups are preferably attached in the 3- and/or 5-position of the pyridine ring. Methyl or methoxy groups are preferred for $R^5$ and $R^6$. When $R^5$ stands for a hydrogen atom, then $R^6$ preferably denotes a methyl or methoxy group attached in the 3- or 5-position of the pyridine ring. B, which may be attached in the 2-, 3- or 4-position of the pyridine ring, preferably in the 2- or 3position, stands for a group of the formula

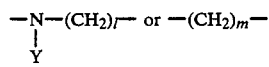

wherein Y denotes a hydrogen atom or a straight chained $C_1$-$C_3$-alkyl group, preferably a methyl, ethyl, n-propyl or isopropyl group, in particular a methyl group; l has the value 2, 3 or 4, preferably 2 or 3, and m has the value 3, 4 or 5, preferably 4.

In embodiment (d), R denotes a group of the formula

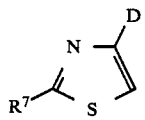

wherein the substituent $R^7$ may be a group of the formula $(R^1R^2)N$—CH₂— wherein $R^1$ and $R^2$, which may be identical or different, preferably denote a straight chained $C_1$-$C_6$-alkyl group, most preferably a straight chained $C_1$-$C_4$-alkyl group, for example a methyl, ethyl or n-propyl group, in particular a methyl group. $R^7$ may also stand for a group of the formula $(H_2N)_2C=N$—,

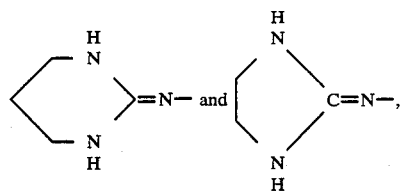

one of the last two mentioned groups being particularly preferred, D denotes a connecting link of the formula —CH₂—S—(CH₂)ₙ— or —(CH₂)ₒ—, wherein n has the value 2 or 3, preferably, 2, and o has the value 2, 3 or 4, preferably 3.

In embodiment (e), R denotes a group of the formula

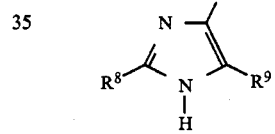

wherein $R^8$ denotes a hydrogen atom or a benzyl group optionally substituted by a halogen atom, for example by a fluorine, bromine or chlorine atom, preferably a chlorine atom, the para-position being preferred. $R^8$ may also stand for a group of the formula $(R^1R^2)N$—CH₂— wherein $R^1$ and $R^2$ have the meanings mentioned above under (a) but they preferably each stand for a methyl group. $R^8$ may also stand for an amino group but $R^8$ is preferably a hydrogen atom. $R^9$ denotes a hydrogen atom, a straight chained $C_1$-$C_3$-alkyl group such as, for example, a methyl or ethyl group, preferably a methyl group, or a $C_1$-$C_3$-alkylthio group, most preferably a methylthio group. When $R^8$ stands for a hydrogen atom and $R^9$ for a methylthio group, then E preferably denotes a group of the formula —CH₂—S—(CH₂)ₙ— wherein n has the value 2 or 3, preferably 2. E may also advantageously denote a group of the formula

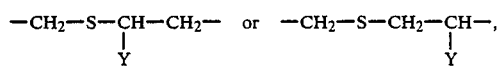

wherein Y stands for a $C_1$-$C_3$-alkyl group, for example a methyl or ethyl group, preferably a methyl group.

In embodiment (f) R denotes a group of the formula

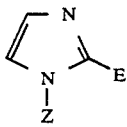

wherein Z denotes a hydrogen atom or a straight chained $C_1$-$C_3$-alkyl group, preferably a methyl group, and E has the same definition as that given in the description of embodiment (e) but preferably stands for the group —$CH_2$—S—$(CH_2)_2$—.

In embodiment (g) R denotes a group of the formula R''—A'—B' wherein R'' stands for a substituted or an unsubstituted phenyl group or a substituted or an unsubstituted naphthyl group. When R'' is a substituted phenyl group or a substituted naphthyl group, then R'' may be represented by one of the following formulae:

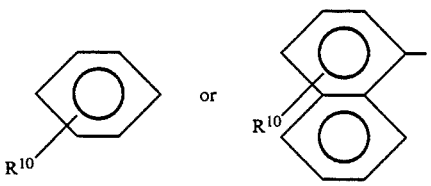

wherein $R^{10}$ denotes a halogen atom preferably bound in the meta- or para-position to A', for example a fluorine, bromine, chlorine or iodine atom, preferably a fluorine or chlorine atom, most preferably a fluorine atom; or it denotes a straight chained $C_1$-$C_3$-alkyl group, for example a methyl or ethyl group, or a straight chained $C_1$-$C_3$-alkoxy group, for example a methoxy group or a trifluoromethyl group. A' stands for a single bond or for a group of the formula —$CR^{1'}R^{2'}$ or for a nitrogen atom which is substituted with an optionally substituted aryl, hetaryl or benzyl group or with a hydrogen atom or a straight chained $C_1$-$C_3$-alkyl group. In the event of substitution, the aryl, hetaryl or benzyl group may be substituted, for example, in the meta- or para-position, preferably in the para-position, with a halogen atom, for example a fluorine, chlorine, bromine or iodine atom, preferably a fluorine atom, or with a straight chained $C_1$-$C_3$-alkyl group, for example a methyl, ethyl or propyl group, preferably a methyl group, or with a straight chained $C_1$-$C_3$-alkoxy group, for example a methoxy, ethoxy or propoxy group, preferably a methoxy group. $R^{1'}$ denotes a hydrogen atom or a methyl group and $R^{2'}$ stands for an unsubstituted or a substituted phenyl group or an unsubstituted or a substituted hetaryl group. The hetaryl group may be, for example, a pyridine ring, a thiophene ring or a furan ring. If the phenyl group or the hetaryl group is substituted, the substituent is preferably a halogen atom, for example a fluorine, bromine, chlorine or iodine atom, preferably a fluorine or chlorine atom, or a straight chained $C_1$-$C_3$-alkyl group, for example a methyl or ethyl group, or a straight chained $C_1$-$C_3$-alkoxy group, for example a methoxy group. B' stands for one of the following groups: —CH(Y)—S—$(CH_2)_{m'}$—, —$CH_2$—S—$CH_2$—CH(Y)—$CH_2$—, —$CH_2$—S—CH(Y)—$CH_2$—, —$CH_2$—S—$CH_2$—CH(Y), —$(CH_2)_{n''}$—, —$CH_2$—CH(Y)—, —$(CH_2)_{n''}$—CH(Y)—, —O—$(CH_2)_2$—, —$CH_2$—O—$(CH_2)_{o'}$—, —$CH_2$—O—$CH_2$—CH(Y)—$CH_2$—, —O—$CH_2$—CH(Y)—, —O—CH(Y)—$CH_2$—, —S—$(CH_2)_q$—, —S—$CH_2$—CH(Y)—, —S—CH(Y)—$CH_2$— or —S—CH(Y)—$CH_2$. In these groups, Y denotes a hydrogen atom or a straight chained $C_1$-$C_3$-alkyl group as defined above in the description of embodiment (c), preferably a methyl group; m' and o' have the value 2 or 3 and n'' and q have the value 2, 3, 4 or 5.

In embodiment (h) R denotes a group of the formula R'''—A''—B''— wherein R''' stands for a substituted or unsubstituted hetaryl group which may carry a condensed phenyl ring. The hetaryl group may be, for example, a pyridine, imidazole, pyrimidine, thiophene, furan, benzimidazole or quinoline ring. The hetaryl ring denoted by R''' may be substituted or unsubstituted. When the hetaryl ring is substituted, R''' may be represented by one of the following formulae:

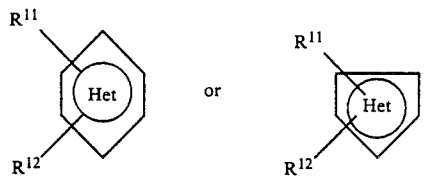

wherein $R^{11}$ and $R^{12}$ denote, independently of one another, a halogen atom, for example a fluorine, bromine, chlorine or iodine atom, preferably a fluorine or chlorine atom, a straight chained $C_1$-$C_3$-alkyl group, for example a methyl, ethyl or propyl group, preferably a methyl group, or a straight chained $C_1$-$C_3$-alkoxy group, preferably a methoxy group. A'' stands for a single bond, for a group of the formula —$CR^{1'}R^{2'}$ or for a nitrogen atom which is substituted with an optionally substituted aryl, hetaryl or benzyl group or with a hydrogen atom or a straight chained $C_1$-$C_3$-alkyl group. The aryl group is preferably a phenyl group. The hetaryl group may be, for example, a pyridine ring, a benzimidazole ring, a thiophene ring or a furan ring. The aryl, hetaryl or benzyl group may, for example, be substituted in the meta- or para-position, preferably in the para-position, with a halogen atom, for example a fluorine, chlorine, bromine or iodine atom, preferably a fluorine or chlorine atom, or with a straight chained $C_1$-$C_3$-alkyl group, for example a methyl, ethyl or propyl group, preferably a methyl group, or with a straight chained $C_1$-$C_3$-alkoxy group, for example a methoxy, ethoxy or propoxy group, preferably a methoxy group.

$R^{1'}$ denotes a hydrogen atom or a methyl group and $R^{2'}$ denotes a substituted or unsubstituted phenyl group or a substituted or unsubstituted hetaryl group. The hetaryl group may be, for example, a benzimidazole ring, a pyridine ring, a thiophene ring or a furan ring. When the phenyl group or the hetaryl group is substituted then the substituent is preferably a halogen atom, for example a fluorine, bromine, chlorine or iodine atom, preferably a fluorine or chlorine atom, a straight chained $C_1$-$C_3$-alkyl group, for example a methyl or ethyl group, or a straight chained $C_1$-$C_3$-alkoxy group, for example a methoxy group. When A'' stands for a single bond then this single bond is arranged in the 2-, 3- or 4-position of the hetaryl group, i.e. it links the group B as defined above with the hetaryl group in the 2-, 3- or 4-position of the hetaryl group. When the hetaryl ring is a benzimidazole ring, the only possible position for the linkage is the 2-position of the benzimidazole ring.

B'' stands for one of the following groups: —CH(Y)—S—$(CH_2)_{m'}$, —$CH_2$—S—$CH_2$—CH(Y)—$CH_2$—, —CH$_2$—S—CH(Y)—CH$_2$—, —CH$_2$—CH(Y)—, —CH$_2$—S—CH$_2$CH(Y)—, —(CH$_2$)$_{n''}$—, —O(CH$_2$)$_{n''}$—, —S—CH$_2$CH(Y)—, S—CH(Y)—CH$_2$—, —S—(CH$_2$)$_q$— or —S—CH$_2$—CH(Y)—CH$_2$—, wherein Y denotes a hydrogen atom or a straight chained C$_1$-C$_3$-alkyl group, m' has the value 2 or 3 and n'' and q have the value 2,3,4 or 5.

In a preferred group of compounds of embodiment (h), the symbol R denotes a group of the formula R'''—A''—B''— wherein R''' stands for a group of the following formula

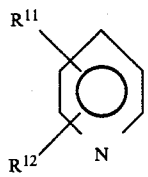

wherein R$^{11}$ and R$^{12}$ denote, independently of one another, a halogen atom, for example a fluorine, chlorine or bromine atom, a straight chained C$_1$-C$_3$-alkyl group, for example a methyl or ethyl group, or a straight chained C$_1$-C$_3$-alkoxy group, for example a methoxy or ethoxy group. A'' preferably stands for a group of the formula —CR$^{1'}$R$^{2'}$ wherein R$^{1'}$ denotes a hydrogen atom or a methyl group and R$^{2'}$ denotes an unsubstituted or a mono- to tri-substituted phenyl group. If the phenyl group is substituted, the substituents may consist in particular of 1 to 3 halogen atoms such as fluorine, chlorine or bromine atoms, preferably fluorine or chlorine atoms, one to three C$_1$-C$_3$-alkyl groups, preferably methyl or ethyl groups, and one to three C$_1$-C$_3$-alkoxy groups, preferably methoxy or ethoxy groups. Mono-substitution and especially di-substitution are preferred. If the phenyl group is mono-substituted, the substituent is preferably in the 4-position, and if it is di-substituted then the substituents are preferably in the 3- and the 4-position or in the 3- and 5-position of the phenyl ring. The trifluoromethyl group and the hydroxyl group are also possible substituents for the phenyl ring.

A'' may consist of a nitrogen atom substituted with an aryl, hetaryl, benzyl or methyl group or with a hydrogen atom. Substitution with an aryl group is preferred, in particular with a phenyl group or a benzyl group.

When A'' stands for a group of the formula CR$^{1'}$R$^{2'}$ then B'' stands for a group of the formula —(CH$_2$)$_n$—, —O(CH$_2$)$_2$— or —SCH$_2$CH$_2$—, preferably —(CH$_2$)$_n$— wherein n has the value 2 or 3. When A'' stands for a nitrogen atom substituted with an aryl, hetaryl, benzyl or methyl group or with a hydrogen atom, then B'' stands for a group of the formula —(CH$_2$)$_n$— wherein n has the value 2 or 3.

In a preferred group of compounds of embodiment (h), R denotes a group of the formula R'''—A''—B'' wherein R''' stands for a group corresponding to the following formula

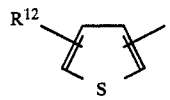

wherein R$^{12}$ denotes a hydrogen atom, a halogen atom, preferably a chlorine atom, a straight chained C$_1$-C$_3$-alkyl group, preferably a methyl group, the group (CH$_3$)$_2$—NCH$_2$— or the group

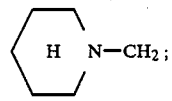

A'' stands for a group of the formula —CR$^{1'}$R$^{2'}$ wherein R$^{1'}$ denotes a hydrogen atom or a methyl group and R$^{2'}$ denotes an unsubstituted or a mono- to tri-substituted phenyl group, or A'' may stand for a nitrogen atom substituted with an aryl, hetaryl, benzyl or methyl group or with a hydrogen atom; and B'' stands for one of the following groups: —CH$_2$—S—CH$_2$—CH$_2$—, —CH$_2$—S—CH$_2$—CH(CH$_3$)—CH$_2$—, —CH$_2$—S—CH(CH$_3$)—CH$_2$— or —CH$_2$—S—CH$_2$—CH(CH$_3$), preferably —CH$_2$—S—CH$_2$—CH$_2$—.

In another preferred group of compounds of embodiment (h), R denotes a group of the formula R'''—A''—B'' wherein R''' denotes a group corresponding to the following formula

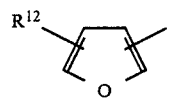

wherein R$^{12}$ denotes a hydrogen atom, a halogen atom, preferably a chlorine atom, a straight chained C$_1$-C$_3$-alkyl group, preferably a methyl group, the group (CH$_3$)$_2$—NCH$_2$— or the group

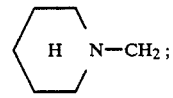

A'' stands for a single bond in the 2-position, and B'' stands for one of the following groups: —CH$_2$—S—CH$_2$—CH$_2$—, —CH$_2$—S—CH$_2$—CH(CH$_3$)—CH$_2$—, —CH$_2$—S—CH(CH$_3$)—CH$_2$— or —CH$_2$—S—CH$_2$—CH(CH$_3$), preferably —CH$_2$—S—CH$_2$—CH$_2$—.

In another preferred group of compounds of embodiment (h), R denotes a group of the formula R'''—A''—B'' wherein R''' denotes a group corresponding to one of the following formulae:

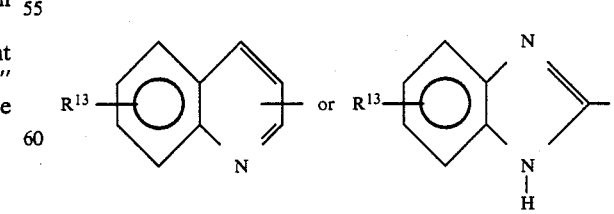

wherein R$^{13}$ denotes a hydrogen atom, a halogen atom, preferably a chlorine atom, a straight chained C$_1$-C$_3$-alkyl group, preferably a methyl group, the group (CH$_3$)$_2$—NCH$_2$ or the group

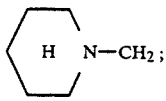

A" stands for a single bond and B" stands for one of the following groups: —CH$_2$—S—CH$_2$—CH$_2$—, —CH$_2$—S—CH$_2$—CH(CH$_3$)—CH$_2$—, —CH$_2$—S—CH(CH$_3$)—CH$_2$— or CH$_2$—S—CH$_2$—CH(CH$_3$), preferably —CH$_2$—S—CH$_2$—CH$_2$—.

The compounds according to the invention corresponding to the general formula I may be prepared by two different process variations:

(1) by the reaction of a compound corresponding to the general formula II

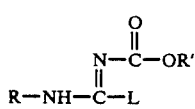
(II)

wherein R and R' have the meanings indicated above and L denotes a removable group, for example a C$_1$-C$_4$-alkylthio, a C$_1$-C$_4$-alkoxy, an arylthio or an aryloxy group, preferably a methylthio group or a phenoxy group, with a compound corresponding to the general formula III

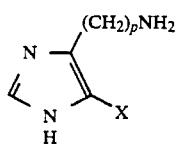
(III)

wherein X and p have the meanings defined above. The reaction is preferably carried out in equimolar quantities and in a polar solvent such as, for example, acetonitrile, dimethylsulphoxide, dimethylformamide or pyridine, preferably in acetonitrile, at temperatures from room temperature to the reflux temperature of the solvent used. When L is an alkylthio or arylthio group, it is advantageous to employ acid catalysis, for example by the addition of catalytic quantities of p-toluene sulphonic acid.

(2) Or by the reaction of a compound corresponding to the general formula IV

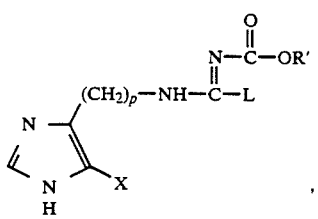
(IV)

wherein R', X and p have the meanings defined above and L has the same meaning as in process variation (1), with a compound corresponding to the general formula V

R—NH$_2$ (V)

wherein R has the meaning indicated above. The quantities and solvents used and the reaction conditions are the same as described above for process variation (1).

The starting compounds of the general formulae II and IV used in both process variations (1) and (2) may be prepared in known manner by methods described in the literature. Compounds corresponding to the general formulae II and IV wherein L stands for an alkoxy or aryloxy group may be prepared, for example, by the reaction of an amine corresponding to the general formula III or V wherein X, p and R have the meanings defined above with a compound corresponding to the general formula VI wherein R' has the meaning indicated above and L stands for an alkoxy or aryloxy group:

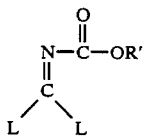
(VI)

Compounds corresponding to the general formulae II and IV in which L stands for an alkylthio or arylthio group may be prepared, for example, by the acylation of a compound corresponding to the general formula VII or VIII

(VII)

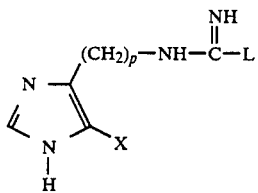
(VIII)

wherein R, X and p have the meanings indicated above and L stands for an alkylthio or arylthio group with a compound corresponding to the general formula IX

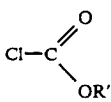
(IX)

wherein R' has the meaning defined above. This reaction is advantageously carried out in the presence of a base such as, for example, a tertiary aliphatic amine such as triethylamine or a heterocyclic amine such as pyridine.

The compounds obtained by the individual process variations are isolated and purified in the usual manner, for example by chromatic methods, recrystallisation, etc.

The compounds obtained in the individual process variations may be converted into their physiologically acceptable salts.

This invention therefore covers not only the tautomeric and stereoisomeric compounds and hydrates of the substances of general formula I but also the physiologically acceptable salts of these compounds. These salts may be formed, for example, with mineral acids such as hydrochloric, hydrobromic or hydriodic acid, phosphoric acid, metaphosphoric acid, nitric acid or sulphuric acid or with organic acids such as formic acid, acetic acid, propionic acid, phenylacetic acid, tartaric acid, citric acid, fumaric acid, methanesulphonic acid, embonic acid, etc.

The compounds according to the invention may be formulated in any desired manner for administration. The invention therefore also covers pharmaceutical preparations which contain at least one compound according to the invention for use in human or veterinary medicine.

Such pharmaceutical preparations may be prepared by the conventional methods using one or more pharmaceutical carriers or diluents.

The compounds according to the invention may therefore be formulated for oral, buccal, topical, parenteral or rectal administration.

For oral administration, the pharmaceutical preparation may be in the form of, for example, tablets, capsules, powders, solutions, syrups or suspensions which have been prepared by the conventional methods using acceptable diluents.

For buccal administration, the pharmaceutical preparation may be in the form of tablets or sachets formulated in the conventional manner.

For parenteral administration, the compounds according to the invention may be formulated for bolus injection or continuous infusion. Formulations for injection may be made up into ampoules containing unit doses or they may be present in multiple dose containers with added preservative.

The pharmaceutical preparations may assume forms such as suspensions, solutions or emulsion in oily or aqueous carriers and they may contain formulating auxiliaries such as suspension or dispersing agents and/or stabilizers.

Alternatively, the active ingredient may be provided in powder form to be reconstituted with a suitable carrier such as sterile, pyrogen-free water before use.

The compounds according to the invention may also be formulated for rectal preparations such as suppositories or retention enemas which may contain, for example, conventional suppository incipients such as cocoa butter or other glycerides.

For topical application, the compounds according to the invention may be formulated as ointments, creams, gels, lotions, powders or sprays in the usual manner.

A suitable daily dose of compounds according to the invention for oral administration may be given in one to four separate doses together containing a total of from 5 mg to 1 g per day, depending on the condition of the patient. In some cases, it may be necessary to deviate from the quantities mentioned, depending on the individual response to the active ingredient or the nature of its formulation and on the time or time interval of administration. In some cases, for example, it may be sufficient to administer less than the minimum quantity indicated above whereas in others it may be necessary to exceed the upper limit.

The guanidine carboxylic acid esters according to the invention corresponding to the general formula I and their pharmacologically acceptable salts show marked cardiotonic effects. When administered orally, they are surprisingly found to be considerably superior to compounds hitherto known which have a similar type of action (see DE 3 512 084, DE 3 528 214, DE 3 528 215 and EP 0 199 845) and they are therefore suitable for the treatment and prevention of cardiac and circulatory diseases. They are found to have an excellent activity in various types of tests, e.g. a strongly positive inotropic action in vivo on guinea pigs.

Haemodynamic characterisation of the positive inotropic action of narcotised guinea pigs (a) Method The animals are narcotised with urethane (1.5 g/kg). The trachea is cannulated for volumetric control of the inspiration. Both carotid arteries are then exposed operatively, and a Tip catherter (3 F) is introduced through the right carotid and moved forwards through the ascending aorta into the left ventricle with continuous registration of the pressure. Successful passage through the aortic valves is indicated by the typical left ventricular pressure curve. A thermistor probe (3 F, F. Edwards) is pushed forwards into the aortic arch via the left carotid for thermodilution. The thermistor probe has a lumen for recording the arterial blood pressure. For application of the cold injectate (0.2 ml of 0.9% NaCl, 15° C.), a catheter is passed through the right jugular vein to be placed in front of the right auricle. The ECG is recorded in the first shunt. The duodenum is exposed in the upper abdominal region by a 1 cm long median section and the test substances are injected into the duodenum by a syringe needle. All substances are suspended in tylose (injection volume 1 ml/kg) and applied after haemodynamic stabilization and under $\beta$ blockage (Metoprolol 2 mg/kg i.m.).

All circulatory parameters are continuously registered on a direct recorder. The contractility (dp/dt) is calculated from the volume/pressure curve. (b) Measured values

| Example No. | Dose mg/kg | Change in contractility dp/dt |
|---|---|---|
| 1 | 2.5 | +50% |
| 2 | 2.5 | +71% |
| 6 | 5 | +158% |
| 7 | 10 | +40% |
| Comparison | 20 | +78% |

Comparison: $N^1$-[3-(Imidazol-4-yl)propyl]-$N^2$-[3-(4-fluorophenyl)-3-(pyridin-2-yl)propyl]-guanidine EPA 199 845 Example 133

EXAMPLE 1

$N^1$-[3-(Imidazol-4-yl)propyl]-$N^2$-[4-(pyridin-2-yl)butyl]-$N^3$-methoxycarbonyl-guanidine

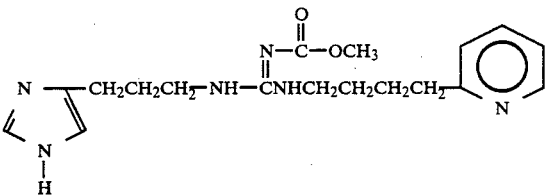

(a) $N^1$-[4-(Pyridin-2-yl)butyl]-$N^2$-methoxycarbonyl-S-methyl isothiourea 2.4 ml (17.1 mmol) of triethylamine are carefully added to a solution of 3.0 g (8.5 mmol) of N-[4-(pyridin-2-yl)butyl]-S-methyl-isothiouronium iodide in 30 ml of dichloromethane which has been cooled to −15° C. 0.66 ml (8.5 mmol) of methyl chloroformate in 20 ml of dichloromethane is then added dropwise with further cooling to keep the reaction temperature below −15° C. After one hour's further stirring at this temperature, the reaction mixture is left to warm up to room temperature and stirring is then continued for 20 hours. The solution is washed twice with 20 ml portions of water. The organic phase is dehydrated with sodium sulphate, filtered and evaporated in vacuo. The crude product obtained is chromatographed on silica gel with dichloromethane/acetone (80:20) for purification. Concentration of the main fraction by evaporation under vacuum yields 2.17 g (90%) of a greenish oil.

C$_{13}$H$_{19}$N$_3$O$_2$S (281.38)

Rf (CH$_2$Cl$_2$/CH$_3$COCH$_3$ 90:10): 0.2

(b) N$^1$-[3-(Imidazol-4-yl)propyl]-N$^2$-[4-(pyridin-2-yl)butyl]-N$^3$-methoxycarbonyl-guanidine 1.00 g (3.5 mmol) of N$^1$-[4-pyridin-2-yl)butyl]-N$^2$-methoxycarbonyl-S-methyl-isothiourea and 0.44 g (3,5 mmol) of 3-(imidazol-4-yl)propylamine are boiled under reflux in 30 ml of acetonitrile for 20 hours. The solvent is evaporated off under vacuum and the residue is chromatographed on silica gel with ethyl acetate/methanol (80:20). 0.43 g (34%) of the title compound is obtained as a colourless oil.

C$_{18}$H$_{26}$N$_6$O$_2$ (358.45)

Rf (CH$_3$COOC$_2$H$_5$/CH$_3$OH 60:40): 0.4

$^1$H-NMR data (CD$_3$OD, TMS as internal standard) δ=1.4–2.1 (m) 6H, 2.5–2.9 (m) 4H, 3.1–3.4 (m) 4H, 3.6 (s) 3H, 5.3 (broad) 3H, replaceable by D$_2$O, 6.8 (s) 1H, 7.1–7.8 (m) 3H, 7.6 (s) 1H, 8.4 (d) 1H ppm.

EXAMPLE 2

N$^1$-[3-(Imidazol-4-yl)propyl]-N$^2$-[4-(pyridin-2-yl)butyl]-N$^3$-ethoxycarbonyl-guanidine

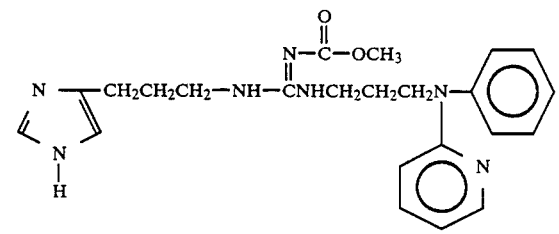

(a) N$^1$-[4-(Pyridin-2-yl)butyl]-N$^2$-ethoxycarbonyl-S-methyl-isothiourea

Prepared by a method analogous to that of Example 1(a) from 7.0 g (20 mmol) of N-[4-(pyridin-2-yl)butyl]-S-methyl-isothiuronium iodide and 1.9 ml (20 mmol) of ethylchloroformate. Chromatographic purification of the crude product on silica gel with dichloromethane-/acetone (9:1) as solvent yields 4.94 g (84%) of a yellowish oil.

C$_{14}$H$_{21}$N$_3$O$_2$S (295.41)

Rf (CH$_2$Cl$_2$/CH$_3$COCH$_3$ 90:10): 0.3

(b) N$^1$-[3-(imidazol-4-yl)propyl]-N$^2$-[4-(pyridin-2-yl)butyl]-N$^3$-ethoxycarbonyl-guanidine 1.75 g (5.9 mmol) of N$^1$-[4-(pyridin-2-yl)butyl]-N$^2$-ethoxycarbonyl-S-methyl-isothiourea and 0.74 g (5.9 mmol) of 3-(imidazol-4-yl)propylamine are boiled for 16 hours in 30 ml of acetonitrile with the addition of 40 mg of p-toluenesulphonic acid. The oil obtained after removal of the solvent by evaporation under vacuum is chromatographed on silica gel with ethyl acetate/methanol (80:20) as solvent. Concentration of the main fraction by evaporation under vacuum yields a colourless oil which crystallises when triturated with diethylether. 0.81 g (37%) of colourless crystals melting at 92° to 94° C. is obtained.

C$_{19}$H$_{28}$N$_6$O$_2$ (372.47)

Rf (CH$_3$COOC$_2$H$_5$/CH$_3$OH 60:40): 0.45

$^1$H-NMR data (CD$_3$OD, TMS as internal standard) δ=1.25 (t) 3H, 1.5–2.0 (m) 6H, 2.65 (t) 2H, 2.8 (t) 2H, 3.1–3.4 (m) 4H, 4.05 (q) 2H, 4.9 (broad) 3H, replaceable by D$_2$O, 6.8 (s) 1H, 7.2–7.9 (m) 3H, 7.6 (s) 1H, 8.5 (d) 1H ppm.

EXAMPLE 3

N$^1$-[3-(Imidazol-4-yl)propyl]-N$^2$-[3-[N-phenyl-N-(pyridin-2-yl)amino]propyl]-N$^3$-methoxycarbonyl-guanidine

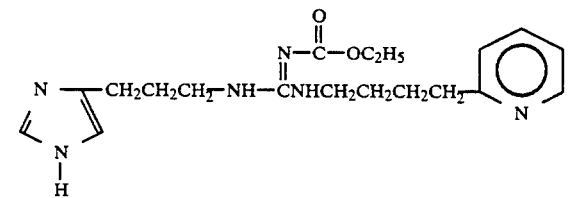

(a) N$^1$-[3-[N-Phenyl-N-(pyridin-2-yl)amino]propyl]-N$^2$-methoxycarbonyl-S-methyl-isothiourea 1.20 g (96%) of the isothiourea is obtained by a method analogous to that of Example 1(a) as a colourless oil from 1.50 g (3.5 mmol) of N-[3-[N-phenyl-N-(pyridin-2-yl)amino]propyl]-S-methyl-isothiuronium iodide and 0.27 ml (3.5 mmol) of methylchloroformate.

C$_{18}$H$_{22}$N$_4$O$_2$S (358.46)

Rf (CH$_2$Cl$_2$/CH$_3$OH 95:5): 0.6

(b) N$^1$-[3-(Imidazol-4-yl)propyl]-N$^2$-[3-[N-phenyl-N-(pyridin-2-yl)amino]propyl]-N$^3$-methoxycarbonyl-guanidine 1.00 g (2.8 mmol) of N$^1$-[3-[N-phenyl-N-(pyridin-2-yl)amino]propyl]-N$^2$-methoxycarbonyl-S-methyl-isothiourea and 0.35 g (2.8 mmol) of 3-(imidazol-4-yl)propylamine are boiled in 30 ml of acetonitrile for 16 hours. The crude product is purified chromatographically on silica gel using ethyl acetate/methanol (90:10) as eluant. 0.50 g (41%) of a colourless, amorphous solid is obtained from the main fraction after concentration by evaporation under vacuum.

C$_{23}$H$_{29}$N$_7$O$_2$ (435.53)

Rf (CH$_3$COOC$_2$H$_5$/CH$_3$OH 60:40): 0.55

$^1$H-NMR data (CD$_3$OD, TMS as internal standard) δ=1.6–2.1 (m) 4H, 2.7 (t) 2H, 3.2–3.5 (m) 4H 3.65 (s) 3H, 4.05 (t) 2H, 5.0 (broad) 3H, replaceable by D$_2$O, 6.3–6.8 (m) 2H, 6.85 (s) 1H, 7.2–7.6 (m) 6H, 7.6 (s) 1H, 8.2 (dd) 1H ppm.

EXAMPLE 4

N$^1$-[3-(Imidazol-4-yl)propyl]-N$^2$-[4-(pyridin-2-ylamino)butyl]-N$^3$-ethoxycarbonyl-guanidine

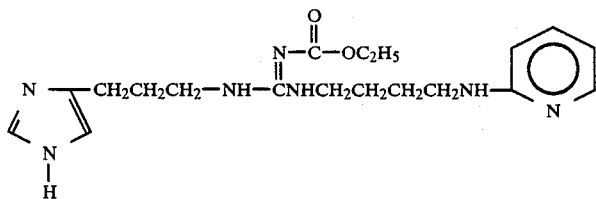 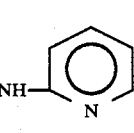

(a) $N^1$-[4-(Pyridin-2-yl-amino)butyl]-$N^2$-ethoxycarbonyl-S-methyl-isothiourea Prepared by a method analogous to that of Example 1(a) from 2.01 g (5.5 mmol) of N-[4-(pyridin-2-yl-amino)butyl]-S-methyl-isothiuronium iodide and 0.52 ml (5.5 mmol) of ethylchloroformate. 1.21 g (71%) of a pale yellow oil which solidifies in the refrigerator is obtained.

$C_{14}H_{22}N_4O_2S$ (310.42)

Rf ($CH_2Cl_2/CH_3OH$ 90:10): 0.6

(b) $N^1$-[3-(Imidazol-4-yl)propyl]-$N^2$-[4-(pyridin-2-yl-amino)butyl]-$N^3$-ethoxycarbonyl-guanidine 1.21 g (3.9 mmol) of $N^1$-[4-(pyridin-2-yl-amino)butyl]-$N^2$-ethoxycarbonyl-S-methyl-isothiourea, 0.48 g (3.9 mmol) of 3-(imidazol-4-yl)propylamine and 40 mg of p-toluenesulphonic acid are boiled in 30 ml of acetonitrile for 14 hours. Chromatographic purification of the crude product on silica gel with ethyl acetate/methanol (90:10→80:20) as solvent yields 0.81 g (53%) of a beige, amorphous solid.

$C_{19}H_{29}N_7O_2$ (387.49)

Rf ($CH_3COOC_2H_5/CH_3OH$ 60:40): 0.5

$^1$H-NMR data ($CD_3OD$, TMS as internal standard) $\delta = 1.25$ (t) 3H, 1.6–2.1 (m) 6H, 2.7 (t) 2H, 3.1–3.5 (m) 6H, 4.15 (q) 2H, 5.0 (broad) 4H, replaceable by $D_2O$, 6.5–6.7 (m) 2H, 6.95 (s) 1H, 7.4–7.6 (m) 1H, 7.8 (s) 1H, 8.0 (dd) 1H ppm.

EXAMPLE 5

$N^1$-[3-(Imidazol-4-yl)propyl]-$N^2$-[3-(4-fluorophenyl)-3-(pyridin-2-yl)propyl]-$N^3$-methoxycarbonyl-guanidine

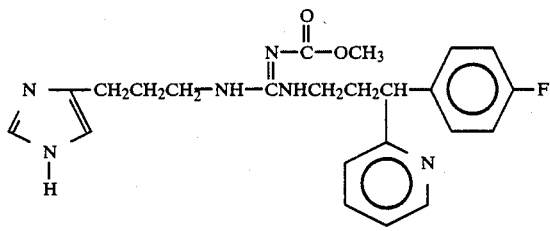

(a) $N^1$-[3-(4-Fluorophenyl)-3-(pyridin-2-yl)-propyl]-$N^2$-methoxycarbonyl-S-methyl-isothiourea 6.5 g (90%) of a colourless oil is obtained by a method analogous to that of Example 1(a) from 8.6 g (20 mmol) of N-[3-(4-fluorophenyl)-3-(pyridin-2-yl)propyl]-S-methyl-isothiuronium iodide and 1.55 ml (20 mmol) of methylchloroformate.

$C_{18}H_{20}FN_3O_2S$ (361.44)

Rf ($CH_2Cl_2/CH_3COCH_3$ 90:10): 0.5

(b) $N^1$-[3-(Imidazol-4-yl)propyl]-$N^2$-[3-(4-fluorophenyl)-3-(pyridin-2-yl)propyl]-$N^3$-methoxycarbonyl-guanidine 1.34 g (3.7 mmol) of $N^1$-[3-(4-fluorophenyl)-3-(pyridin-2-yl)-propyl]-$N^2$-methoxycarbonyl-S-methyl-isourea and 0.46 g (3.7 mmol) of 3-(imidazol-4-yl)propylamine are boiled in 30 ml of acetonitrile for 14 hours with the addition of 30 mg of p-toluenesulphonic acid. The solvent is evaporated off under vacuum and the residue is chromatographed on silica gel with ethyl acetate/methanol (90:10). Concentration of the main fraction by evaporation under vacuum yields 0.91 g (56%) of a colourless, amorphous solid.

$C_{23}H_{27}FN_6O_2$ (438.51)

Rf ($CH_3COOC_2H_5/CH_3OH$ 60:40): 0.45

$^1$H-NMR data ($CD_3OD$, TMS as internal standard) $\delta = 1.7$–2.1 (quin) 2H, 2.2–2.8 (m) 4H, 3.1–3.5 (m) 4H, 3.7 (s) 3H, 4.25 (t) 1H, 5.3 (broad) 3H, replaceable by $D_2O$, 6.9–7.9 (m) 9H, 8.6 (dd) 1H ppm.

EXAMPLE 6

$N^1$-[3-(Imidazol-4-yl)propyl]-$N^2$-[3-(4-fluorophenyl)-3-(pyridin-2-yl)propyl]-$N^3$-ethoxycarbonyl-guanidine

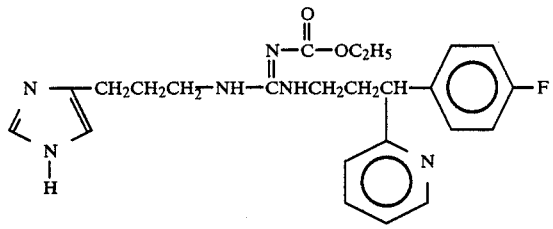

(a) $N^1$-[3-(4-Fluorophenyl)-3-(pyridin-2-yl)-propyl]-$N^2$-ethoxycarbonyl-O-phenyl-isourea 1.40 g (4.9 mmol) of N-(ethoxycarbonyl)-imidocarbonic acid diphenylester are cooled to 5° C. in 20 ml of tetrahydrofuran. 1.13 g (4.9 mmol) of 3-(4-fluorophenyl)-3-(pyridin-2-yl)-propylamine in 20 ml of tetrahydrofuran are added dropwise with cooling over a period of 15 minutes. After four hours' stirring at room temperature, the solution is concentrated by evaporation under vacuum. The colourless oil obtained is used for further reactions without purification.

$C_{24}H_{24}FN_3O_3$ (421.47)

Rf ($CH_2Cl_2/CH_3OH$ 95:5): 0.7

(b) $N^1$-[3-(Imidazol-4-yl)propyl]-$N^2$-[3-(4-fluorophenyl)-3-(pyridin-2-yl)-propyl]-$N^3$-ethoxycarbonyl-guanidine 0.61 g (4.9 mmol) of 3-(imidazol-4-yl)propylamine are added to a solution of 2.06 g (4.9 mmol) of crude $N^1$-[3-(4-fluorophenyl)-3-(pyridin-2-yl)-propyl]-$N^2$-ethoxycarbonyl-O-phenyl-isourea in 40 ml of acetonitrile and the reaction mixture is boiled under reflux for 7 hours. The solvent is concentrated by evaporation under vacuum and the oily residue is chromatographed on silica gel with ethyl acetate/methanol (80:20). Concentration of the main fraction by evaporation under vacuum yields 0.99 g (45%) of a colourless oil.

$C_{24}H_{29}FN_6O_2$ (452.53)

Rf ($CH_3COOC_2H_5/CH_3OH$ 60:40): 0.6

$^1$H-NMR data ($CD_3OD$, TMS as internal standard) $\delta = 1.2$ (t) 3H, 1.7–2.1 (quin) 2H, 2.2–2.8 (m) 4H, 3.1–3.5

(m) 4H, 4.1 (q) 2H, 4.2 (t) 1H, 4.9 (broad) 3H, replaceable by D₂O, 6.8–7.9 (m) 9H, 8.55 (dd) 1H ppm.

EXAMPLE 7

$N^1$-[3-(Imidazol-4-yl)propyl]-$N^2$-[3-(4-fluorophenyl)-3-(pyridin-2-yl)propyl]-$N^3$-butoxycarbonyl-guanidine

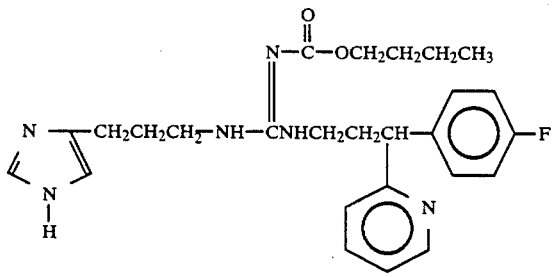

(a) $N^1$-[3-(4-Fluorophenyl)-3-(pyridin-2-yl)-propyl]-$N^2$-butoxycarbonyl-O-phenyl-isourea Prepared by a method analogous to that of Example 6(a) from 3.13 g (10 mmol) of N-butoxycarbonyl-imidocarbonic acid diphenylester and 2.30 g (10 mmol) of 3-(4-fluorophenyl)-3-(pyridin-2-yl)-propylamine in tetrahydrofuran. The product is not isolated but used in solution for further reaction.

$C_{26}H_{28}FN_3O_3$ (449.52)

Rf (CH₂Cl₂/CH₃OH 95:5): 0.85.

(b) $N^1$-[3-(Imidazol-4-yl)propyl]-$N^2$-[3-(4-fluorophenyl)-3-(pyridin-2-yl)propyl]-$N^3$-butoxycarbonyl-guanidine 1.25 g (10 mmol) of 3-(Imidazol-4-yl)propylamine are added to a solution of 4.49 g (10 mmol) of crude $N^1$-[3-(4-fluorophenyl)-3-(pyridin-2-yl)-propyl]-$N^2$-butoxycarbonyl-O-phenyl-isourea in 60 ml of tetrahydrofuran and the mixture is boiled under reflux for 8 hours. The oil obtained after evaporation of the solvent under vacuum is chromatographed on silica gel with ethyl acetate/methanol (80:20) as solvent. 1.40 g (29%) of a colourless, amorphous solid is obtained from the main fraction.

$C_{26}H_{33}FN_6O_2$ (480.59)

Rf (CH₃COOC₂H₅/CH₃OH 60:40): 0.65

¹H-NMR data (CDCl₃, TMS as internal standard) δ=0.95 (t) 3H, 1.1–2.9 (m) 10H, 3.2–3.8 (m) 4H, 4.0–4.3 (2t) 3H, 6.9–7.8 (m) 9H, 8.7 (d) 1H, 9.3 (broad) 1H, replaceable by D₂O, 10.6 (broad) 1H, replaceable by D₂O ppm.

EXAMPLE 8

$N^1$-[3-(Imidazol-4-yl)propyl]-$N^2$-[3-(4-fluorophenyl)-3-(pyridin-2-yl)propyl]-$N^3$-phenoxycarbonyl-guanidine

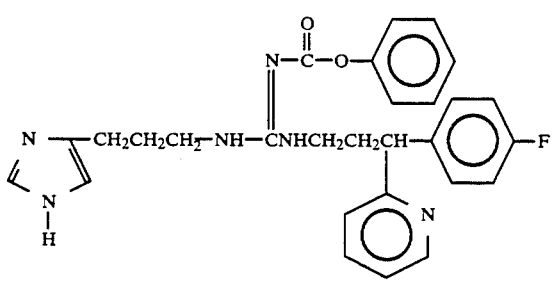

(a) $N^1$-[3-(4-Fluorophenyl)-3-(pyridin-2-yl)-propyl]-$N^2$-phenoxycarbonyl-O-phenyl-isourea 3.33 g (10 mmol) of N-(Phenoxycarbonyl)-imidocarbonic acid diphenylester and 2.30 g (10 mmol) of 3-(4-fluorophenyl)-3-(pyridin-2-yl)-propylamine are reacted together in 60 ml of acetonitrile by a method analogous to that of Example 6(a). After 5 hours' stirring at room temperature, the compound is used for further reaction in solution without being isolated.

$C_{28}H_{24}FN_3O_3$ (469.51)

(b) $N^1$-[3-(Imidazol-4-yl)propyl]-$N^2$-[3-(4-fluorophenyl)-3-(pyridin-2-yl)-propyl]-$N^3$-phenoxycarbonyl-guanidine 1.25 g (10 mmol) of 3-(Imidazol-4-yl)propylamine are added to the solution obtained in Example 8(a) of 4.69 g (10 mmol) of $N^1$-[3-(4-fluorophenyl)-3-(pyridin-2-yl)propyl]-$N^2$-phenoxycarbonyl-O-phenyl-isourea in acetonitrile and the reaction mixture is boiled for 6 hours. The crude product is chromatographed on silica gel with ethyl acetate/methanol (80:20). 3.65 g (73%) of a colourless, amorphous solid are obtained from the main fraction.

$C_{28}H_{29}FN_6O_2$ (500.57)

Rf (CH₃COOC₂H₅/CH₃OH 80:20): 0.6

¹H-NMR data (d₆-DMSO, TMS as internal standard) δ=1.7 (quin) 2H, 2.1–2.8 (m) 4H, 2.8–3.5 (m) 4H, 4.3 (t) 1H, 6.7–7.9 (m) 15H, 1H replaceable by D₂O, 8.7 (dd) 1H, 9.5 (t) 1H, replaceable by D₂O ppm.

EXAMPLE 9

$N^1$-[3-(Imidazol-4-yl)propyl]-$N^2$-[3-(4-fluorophenyl)-3-(pyridin-2-yl)propyl]-$N^3$-benzyloxycarbonyl-guanidine

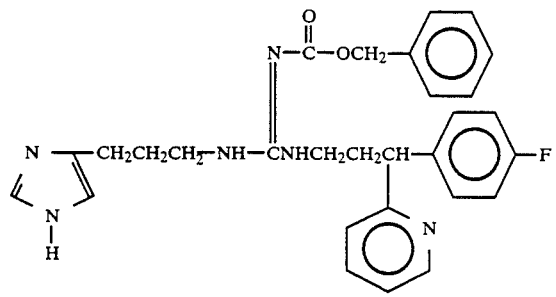

(a) $N^1$-[3-(4-Fluorophenyl)-3-(pyridin-2-yl)-propyl]-$N^2$-benzyloxycarbonyl-S-methyl-isothiourea Obtained as a pale yellow oil by a method analogous to that of Example 1(a) from 2.16 g (5 mmol) of N-[3-(4-fluorophenyl)-3-(pyridin-2-yl)-propyl]-S-methyl-isothiuronium iodide and 0.71 ml (5 mmol) of benzylchloroformate after chromatography on silica gel with dichloromethane/acetone (95:5) as solvent.

Yield: 1.55 g (71%). $C_{24}H_{24}FN_3O_2S$ (437.54)

Rf (CH₂Cl₂/CH₃COCH₃ 95:5): 0.7

(b) $N^1$-[3-(Imidazol-4-yl)propyl]-$N^2$-[3-(4-fluorophenyl)-3-(pyridin-2-yl)propyl]-$N^3$-benzyloxycarbonyl-guanidine 1.23 g (2.8 mmol) of $N^1$-[3-(4-fluorophenyl)-3-(pyridin-2-yl)-propyl]-$N^2$-benzyloxycarbonyl-S-methyl-isothiourea and 0.35 g (2.8 mmol) of 3-(imidazol-4-yl)propylamine are boiled in 25 ml of acetonitrile for 24 hours. When the crude product obtained by removal of the solvent by evaporation under vacuum is chromatographically purified on silica gel with ethyl acetate/methanol (80:20) as solvent, 0.58 g (40%) of a colourless, amorphous solid is obtained.

$C_{29}H_{31}FN_6O_2$ (514.60)

Rf (CH₃COOC₂H₅/CH₃OH 80:20): 0.5

¹H-NMR data (CDCl₃, TMS as internal standard) δ=1.7–2.9 (m) 6H, 3.1–3.7 (m) 4H, 4.1–4.3 (m) 1H, 5.2 (s) 2H, 6.85 (s) 1H, 6.9–7.8 (m) 14H, 1H replaceable by D₂O, 8.7 (dd) 1H, 9.3 (broad) 1H, replaceable by D₂O ppm.

EXAMPLE 10

N¹-[3-(Imidazol-4-yl)propyl]-N²-[2-[N-(4-chlorobenzyl)-N-(pyridin-2-yl)amino]ethyl]-N³-ethoxycarbonyl-guanidine

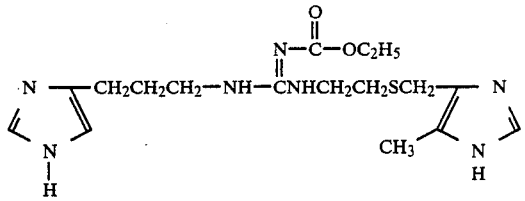

(a) N¹-[2-[[(1-Ethoxycarbonyl-5-methyl-imidazol-4-

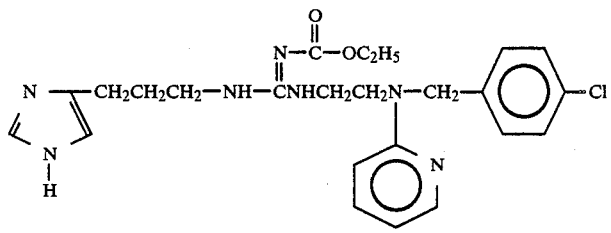

(a) N¹-[2-[N-(4-Chlorobenzyl)-N-(pyridin-2-yl)amino]ethyl]-N²-ethoxycarbonyl-S-methyl-isothiourea Prepared by a method analogous to that of Example 1(a) from 1.50 g (3.2 mmol) of N-[2-[N-(4-chlorobenzyl)-N-(pyridin-2-yl)amino]ethyl]-S-methyl-isothiuronium iodide and 0.31 ml (3.2 mmol) of ethyl chloroformate. 1.20 g (91%) of a colourless oil.

C₁₉H₂₃ClN₄O₂S (406.93)

Rf (CH₂Cl₂/CH₃COCH₃ 99:1): 0.4

(b) N¹-[3-(Imidazol-4-yl)propyl]-N²-[2-[N-(4-chlorobenzyl)-N-(pyridin-2-yl)-amino]ethyl]-N³-ethoxycarbonyl-guanidine 1.02 g (2.5 mmol) of N¹-[2-[N-(4-chlorobenzyl)-N-(pyridin-2-yl)-amino]-ethyl]-N²-ethoxycarbonyl-S-methyl-isothiourea and 0.31 g (2.5 mmol) of 3-(imidazol-4-yl) propylamine are boiled in 20 ml of acetonitrile for 24 hours. The crude product is purified by column chromatography on silica gel with ethyl acetate/methanol (80:20) as solvent. Concentration of the main fraction by evaporation under vacuum yields a colourless oil which is crystallized with 5 ml of ethyl acetate/methanol (80:20). 0.42 g (35%) of colourless crystals melting at 94°–96° C. is obtained.

C₂₄H₃₀ClN₇O₂ (484.00)

Rf (CH₃COOC₂H₅/CH₃OH/NH₃ conc. 80:15:5): 0.55

¹H-NMR data (CD₃OD, TMS as internal standard) δ=1.25 (t) 3H, 1.9 (quin) 2H, 2.7 (t) 2H, 3.2–3.9 (m) 6H, 4.1 (q) 2H, 4.8 (s) 2H, 4.9 (broad) 3H, replaceable by D₂O, 6.6–6.9 (m) 3H, 7.2–7.7 (m) 6H, 8.2 (dd) 1H ppm.

EXAMPLE 11

N¹-[3-(Imidazol-4-yl)propyl]-N²-[2-[[(5-methyl-imidazol-4-yl)methyl]thio]ethyl]-N³-ethoxycarbonyl-guanidine yl)methyl]thio]ethyl]-N²-ethoxycarbonyl-S-methyl-isothiourea 7.8 g (20.9 mmol) of N-[2-[[(5-methyl-imidazol-4-yl)methyl]thio]ethyl]-S-methyl-isothiuronium iodide are reacted with 4.0 ml (41.8 mmol) of ethyl chloroformate and 8.7 ml (62.7 mmol) of triethylamine by a method analogous to that of Example 1(a). The crude product obtained after extraction and concentration of the organic phase by evaporation is chromatographed on silica gel with dichloromethane/acetone (90:10). Concentration of the main fraction by evaporation then yields a colourless oil which crystallises spontaneously. 4.5 g (55%) of colourless crystals melting at 75°–76° C. are obtained.

C₁₅H₂₄N₄O₄S₂ (388.51)

Rf (CH₂Cl₂/CH₃COCH₃ 90:10): 0.4

(b) N¹-[3-(Imidazol-4-yl)propyl]-N²-[2-[[(5-methyl-imidazol-4-yl)methyl]thio]ethyl]-N³-ethoxycarbonyl-guanidine 4.0 g (10.3 mmol) of N¹-[2-[[(1-Ethoxycarbonyl-5-methyl-imidazol-4-yl)methyl]thio]ethyl]-N²-ethoxycarbonyl-S-methyl-isothiourea, 1.3 g (10.3 mmol) of 3-(imidazol-4-yl) propylamine and 0.1 g of p-toluenesulphonic acid in 100 ml of acetonitrile are boiled for 16 hours. The solvent is evaporated off under vacuum and the residue is chromatographed on silica gel with ethyl acetate/methanol (60:40) as solvent. Concentration of the polar main fraction by evaporation under vacuum yields 1.1 g (27%) of a colourless, amorphous solid.

C₁₇H₂₇N₇O₂S (393.51)

Rf (CH₃COOC₂H₅/CH₃OH 60:40): 0.5

¹H-NMR data (CD₃OD, TMS as internal standard) δ=1.2 (t) 3H, 1.9 (quin) 2H, 2.2 (s) 3H, 2.7 (t) 4H, 3.2–3.6 (m) 4H, 3.8 (s) 2H, 4.1 (q) 2H, 5.2 (broad) 4H, replaceable by D₂O, 6.9 (s) 1H, 7.6 (s) 1H, 7.7 (s) 1H, ppm.

EXAMPLE 12

N¹-[3-(3,4-dichlorophenyl)-3-(pyridin-2-yl)propyl]-N²-ethoxycarbonyl-N³-[3-(1H-imidazol-4-yl)propyl]-guanidine

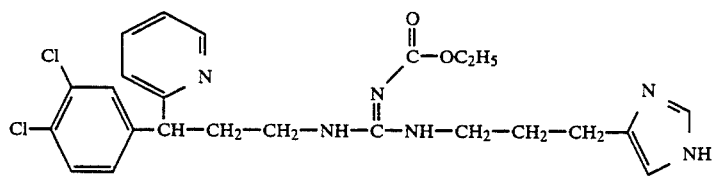

1.41 g (5 mmol) of 3-(3,4-dichlorophenyl)-3-(pyridin-2-yl)propylamine and 1.43 g (5 mmol) of N-ethoxycarbonyl-diphenylimidocarbonate are stirred in 20 ml of acetonitrile for 20 minutes at room temperature. After the addition of 0.65 g (5.2 mmol) of 3-(1H-imidazol-4-yl)propylamine the reaction mixture is heated under reflux for 10 hours and then concentrated by evaporation under vacuum. The residue is taken up with a 5% hydrochloric acid solution and extracted with ether. After the extract has been made alkaline with ammonia, it is extracted with methylene chloride and the organic phase is washed with water, dehydrated over sodium sulphate and concentrated by evaporation under vacuum. The reaction product is isolated by chromatography on silica gel 60 $PF_{254}$ containing gypsum (solvent: chloroform/methanol, 99.5/0.5, ammoniacal atmosphere). After concentration of the eluate by evaporation, the amorphous solid initially obtained (1.4 g, 56%) is crystallized from ethyl acetate/ether. M.p. 73°–75° C.

$C_{24}H_{28}Cl_2N_6O_2$ (503.4) Analysis: calculated: C 57.26 H 5.61 N 16.69 found: C 57.04 H 5.78 N 16.29

MS (FAB method): m/z (rel. Int (%))=503 ([M+H]+, 9), 264 (73), 109 (100), 95 (31).

1H-NMR data: (d$_6$-DMSO, TMS as internal standard) δ=1.13 (t) 3H 1.75 (m) 2H 2.25 (m) 1H 2.43 (m) 1H 2.5 (m, partially covered) 2H 3.10 (m) 2H 3.16 (m) 2H 3.88 (q) 2H 4.20 (t) 1H 6.6–7.2 (broad) 2H, 1H replaceable by D$_2$O 7.23 (m) 1H 7.35–7.8 (m) 6H 8.54 (d) 1H 8.9 (broad) 1H, replaceable by D$_2$O 11.8 (broad) 1H replaceable by D$_2$O, ppm

EXAMPLE 13

N$^1$-[3-(3,4-difluorophenyl)-3-(pyridin-2-yl)propyl]-N$^2$-ethoxycarbonyl-N$^3$-[3-(1H-imidazol-4-yl)propyl]-guanidine.

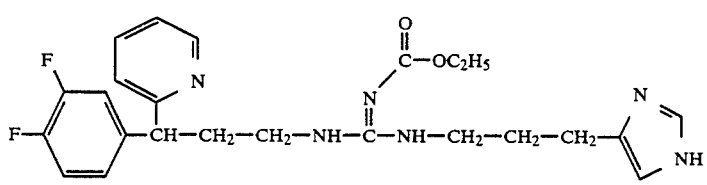

The method of preparation is analogous to that of Example 12, starting with 1.24 g (5 mmol) of 3-(3,4-difluorophenyl)-3-(pyridin-2-yl)propylamine. Yield: 1.2 g (51%) of colourless crystals melting at 119° to 120° C. (ethyl acetate/ether). $C_{24}H_{28}F_2N_6O_2$ (470.5)

Analysis: calculated: C 61.27 H 6.00 N 17.86 found: C 61.14 H 6.22 N 17.57

MS (FAB method): m/z (rel. Int. (%))=471 ([M+H]+, 8), 425 (4), 323 (100), 204 (19), 109 (69), 95 (15), 81 (25).

1H-NMR data: (d$_6$-DMSO, TMS as internal standard) δ=1.13 (t) 3H 1.75 (m) 2H 2.24 (m) 1H 2.44 (m) 1H 2.5 (m, partially covered) 2H 3.08 (m) 2H 3.17 (m) 2H 3.88 (q) 2H 4.18 (t) 1H 6.6–7.2 (broad) 2H, 1H replaceable by D$_2$O 7.2–7.6 (m) 6H 7.71 (m) 1H 8.54 (d) 1H 8.9 (broad) 1H, replaceable by D$_2$O 11.8 (broad) 1H, replaceable by D$_2$O ppm

EXAMPLE 14

N$^1$-[3-(3,5-difluorophenyl)-3-(pyridin-2-yl)propyl]-N$^2$-ethoxycarbonyl-N$^3$-[3-(1H-imidazol-4-yl)propyl]-guanidine.

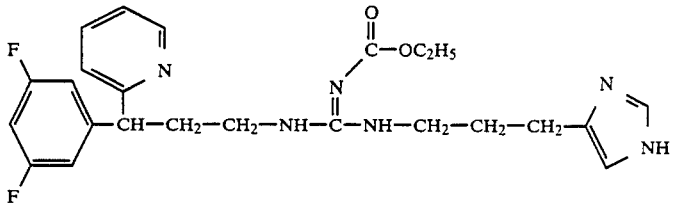

The method of preparation is analogous to that of Example 12, starting from 1.24 g (5 mmol) of 3-(3,5-difluorophenyl)-3-(pyridin-2-yl)propylamine. Yield: 1.3 g (55%) of colourless crystals melting at 104° to 105° C. (ethyl acetate/ether).

$C_{24}H_{28}F_2N_6O_2$ (470.5) Analysis: calculated: C: 61.27; H: 6.00; N: 17.86; found: C: 60.95; H: 6.08; N: 17.63.

MS (FAB method): m/z (rel. Int. (%))=471 ([M+H]+, 9), 232 (100), 204 (17), 172 (11), 109 (66), 95 (15).

1H-NMR data: (d$_6$-DMSO, TMS as internal standard) δ=1.13 (t) 3H 1.76 (m) 2H 2.2–2.6 (m) 4H 3.10 (m) 2H 3.16 (m) 2H 3.91 (q) 2H 4.21 (t) 1H 6.77 (broad) 1H 6.9 (broad) 1H replaceable by D$_2$O 7.0–7.45 (m) 5H 7.50 (s) 1H 7.71 (m) 1H 8.55 (d) 1H 8.9 (broad) 1H replaceable by D$_2$O 11.85 (broad) 1H replaceable by D$_2$O, ppm

EXAMPLE 15

N[1]-[3-(4-fluorophenyl)-3-(pyridin-3-yl)propyl]-N[2]-ethoxycarbonyl-N[3]-[3-(1H-imidazol-4-yl)propyl]-guanidine.

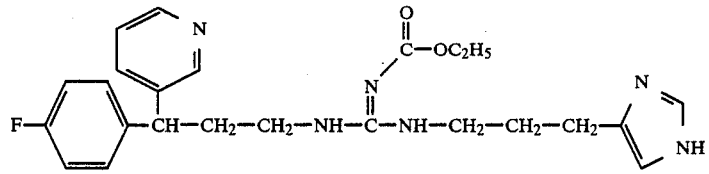

The method of preparation is analogous to that of Example 12, starting from 1.15 g (5 mmol) of 3-(4-fluorophenyl)-3-(pyridin-3-yl)propylamine. Yield: 1.15 g (47%) of colourless crystals melting at 104° to 105° C. (ethyl acetate/ether).

$C_{24}H_{29}FN_6O_2$ (452.5) Analysis: calculated: C: 63.70; H: 6.46; N: 18.57; found: C: 63.33; H: 6.65; N: 18.39.

$^1$H-NMR data: (d$_6$-DMSO, TMS as internal standard) δ=1.13 (t) 3H 1.75 (m) 2H 2.29 (m) 2H 2.5 (m, partially covered) 2H 3.09 (m) 2H 3.16 (m) 2H 3.88 (q) 2H 4.08 (t) 1H 6.77 (broad) 1H 7.0 (very broad) 1H, replaceable by D$_2$O 7.12 (dd) 2H 7.30 (dd) 1H 7.40 (dd) 2H 7.50 (s) 1H 7.77 (d) 1H 8.40 (d) 1H 8.56 (s) 1H 8.95 (broad) 1H, replaceable by D$_2$O 18.4 (broad) 1H, replaceable by D$_2$O ppm,

EXAMPLE 16

N[1]-[(1,1-dimethylethyl)oxycarbonyl]-N[2]-[3-(4-fluorophenyl)-3-(pyridin-2-yl)propyl]-N[3]-[3-(1H-imidazol-4-yl)propyl]guanidine

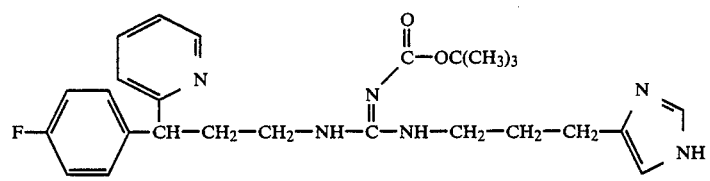

The method of preparation is analogous to that of Example 12, starting from 1.15 g (5 mmol) of 3-(4-fluorophenyl)-3-pyridin-2-yl)propylamine, 1.57 g (5 mmol) of N-tert.-butoxycarbonyldiphenylimidocarbonate and 0.65 g (5.2 mmol) of 3-(1H-imidazol-4-yl)propylamine. Yield: 1.1 g (46%) of colourless crystals, m.p. 116° to 117° C. (ethyl acetate/ether).

$C_{26}H_{33}FN_6O_2$ (480.6) Analysis: calculated: C: 64.98; H: 6.92; N: 17.49; found: C: 65.01; H: 7.17; N: 17.56.

MS (FAB method): m/z (rel. Int. [%])=481 ([M+H]$^+$, 6), 381 (39), 214 (100), 186 (29), 151 (12), 109 (90), 100 (45), 95 (22), 82 (31), 81 (39), 57 (88).

$^1$H-NMR data: (d$_6$-DMSO, TMS as internal standard) δ=1.37 (s) 9H 1.74 (m) 2H 2.21 (m) 1H 2.35–2.6 (m) 3H 3.06 (m) 2H 3.17 (m) 2H 4.17 (t) 1H 6.76 (s) 1H 6.9 (broad) 1H, replaceable by D$_2$O 7.10 (dd) 2H 7.20 (dd) 1H 7.32 (d) 1H 7.40 (dd) 2H 7.49 (s) 1H 7.69 (dd) 1H 8.53 (d) 1H 8.9 (broad) 1H, replaceable by D$_2$O 11.9 (broad) 1H, replaceable by D$_2$O ppm

EXAMPLE 17

N[1]-ethoxycarbonyl-N[2]-[3-(1H-imidazol-4-yl)propyl]-N[3]-[2-phenyl-2-(2-pyridyl)ethyl]guanidine.

The method of preparation is analogous to that of Example 12, starting with 0.99 g (5 mmol) of 2-phenyl-2-(2-pyridyl)ethylamine. Yield: 0.6 g (27%) of colourless crystals, m.p. 145° C. (ethyl acetate/ethanol).

$C_{23}H_{28}N_6O_2$ (420.5) MS (FAB method): m/z (rel. Int. [%])=421 ([M+H]$^+$, 13), 394 (6), 375 (8), 182 (100), 180 (38), 169 (25), 168 (21), 162 (29), 109 (65), 95 (10), 81 (25).

$^1$H-NMR data: (d$_6$-DMSO, TMS as internal standard) δ=1.11 (m) 3H 1.67 (m) 2H 2.45 (m) 2H 3.0–4.05 (broad) 6H 4.45 (broad) 1H 6.73 (s) 1H 7.1 (broad) 1H, replaceable by D$_2$O 7.15–7.45 (m) 7H 7.50 (s) 1H 7.70 (m) 1H 8.55 (m) 1H 8.90 (broad) 1H, replaceable by D$_2$O 13.43 (broad) 1H, replaceable by D$_2$O, ppm

EXAMPLE 18

N[1]-ethoxycarbonyl-N[2]-[3-(4-fluorophenyl)-3-phenylpropyl]-N[3]-[3-(1H-imidazol-4-yl)propyl]-guanidine.

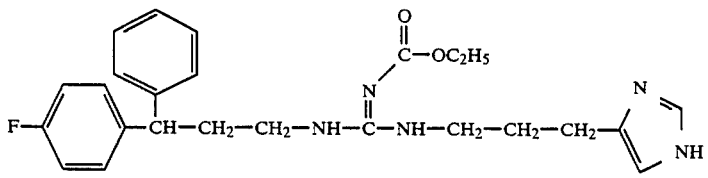

The method of preparation is analogous to that of Example 12, starting from 1.15 g (5 mmol) of 3-(4-fluorophenyl)-3-phenylpropylamine. Yield: 1.1 g (49%) of colourless crystals, m.p. 131° C. (ethyl acetate/ether).

$C_{25}H_{30}FN_5O_2$ (451.5) Analysis: calculated: C: 66.50; H: 6.70; N: 15.51; found: C: 66.32; H: 6.87; N: 15.31.

MS (FAB method): m/z (rel. Int. [%])=452 ([M+H]+, 6), 406 (4), 185 (20), 109 (100), 95 (18), 91 (20)

$^1$H-NMR data: (d$_6$-DMSO, TMS as internal standard) δ=1.13 (t) 3H 1.75 (m) 2H 2.2–2.35 (m) 2H 2.5 (m, partially covered) 2H 3.08 (m) 2H 3.17 (m) 2H 3.89 (q) 2H 4.01 (t) 1H 6.6–7.1 (broad) 2H, 1H replaceable by D$_2$O 7.1–7.4 (m) 9H 7.49 (s) 1H 8.9 (broad) 1H, replaceable by D$_2$O 11.8 (broad) 1H, replaceable by D$_2$O, ppm atmosphere). The amorphous solid (0.9 g, 42%) obtained after evaporation of the eluates crystallizes from ethyl acetate/ether as colourless crystals, m.p. 125° to 126° C.

$C_{25}H_{31}N_5O_2$ (433.6) Analysis: calculated: C: 69.26; H: 7.21; N: 16.15; found: C: 69.30 H: 7.43; N: 16.24.

$^1$H-NMR data (d$_6$-DMSO, TMS as internal standard) δ=1.13 (t) 3H 1.75 (m) 2H 2.28 (m) 2H 2.5 (m, partially covered) 2H 3.09 (m) 2H 3.17 (m) 2H 3.89 (q) 2H 3.99 (t) 1H 6.76 (broad) 1H 7.0 (broad) 1H, replaceable by D$_2$O 7.1–7.35 (m) 10H 7.49 (s) 1H 8.95 (broad) 1H, replaceable by D$_2$O 11.9 (broad) 1H, replaceable by D$_2$O, ppm

EXAMPLE 20

$N^1$-ethoxycarbonyl-$N^2$-[3-(1H-imidazol-4-yl)propyl]-$N^3$-{2-[(pyridin-2-yl)methylthio]ethyl}guanidine.

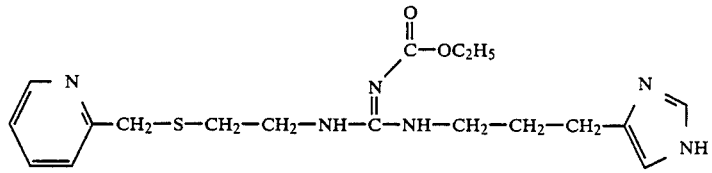

EXAMPLE 19

$N^1$-(3,3-diphenylpropyl)-$N^2$-ethoxycarbonyl-$N^3$-[3-(1H-imidazol-4-yl)propyl]-guanidine.

The method of preparation is analogous to that of Example 19, starting from 1.85 g (5 mmol) of N-{2-[(pyridin-2-yl)methylthio]ethyl}-S-methyl-isothi-

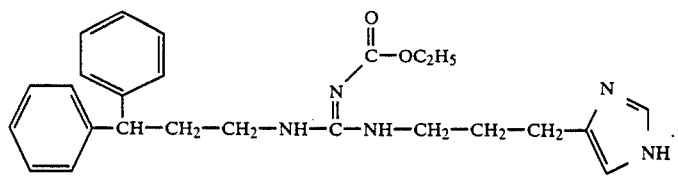

The method of preparation is analogous to that of Example 1, starting from 2.06 g (5 mmol) of N-(3,3-diphenylpropyl)-S-methyl-isothiuronium iodide. The solution is methylene chloride of $N^1$-(3,3-diphenylpropyl)-$N^2$-ethoxycarbonyl-S-methylisothiourea prepared by a method analogous to that of Example 1a was washed with water, dehydrated over sodium sulphate and concentrated by evaporation under vacuum and the residue was taken up with 20 ml of acetonitrile. After the addition of 0.65 g (5.2 mmol) of 3-(1H-imidazol-4-yl)propylamine, the reaction mixture was heated under reflux for 20 hours and concentrated by evaporation under vacuum and the product was isolated by chromatography on silica gel 60 PF$_{254}$ containing gypsum (eluting solvent: chloroform/ethanol, 98+2, ammoniacal uronium iodide. Yield: 1.3 g (54%) of colourless crystals, m.p. 60° to 61° C. (ethyl acetate/ether).

$C_{18}H_{26}N_6O_2S$ (390.5) Analysis: calculated: C: 55.36; H: 6.71; N: 21.52; found: C: 55.37; H: 7.01; N: 21.23.

$^1$H-NMR data: (d$_6$-DMSO, TMS as internal standard) δ=1.14 (t) 3H 1.77 (m) 2H 2.51 (m) 2H 2.62 (m) 2H 3.19 (m) 2H 3.38 (m) 2H 3.84 (s) 2H 3.93 (q) 2H 6.77 (s) 1H 7.2 (very broad) 1H, replaceable by D$_2$O 7.26 (dd) 1H 7.44 (d) 1H 7.53 (s) 1H 7.75 (dd) 1H 8.48 (d) 1H 9.0 (broad) 1H, replaceable by D$_2$O 11.8 (broad) 1H, replaceable by D$_2$O, ppm

EXAMPLE 21

$N^1$-ethoxycarbonyl-$N^2$-[3-(1H-imidazol-4-yl)propyl]-$N^3$-{2-[(pyridin-3-yl)methylthio]ethyl}guanidine.

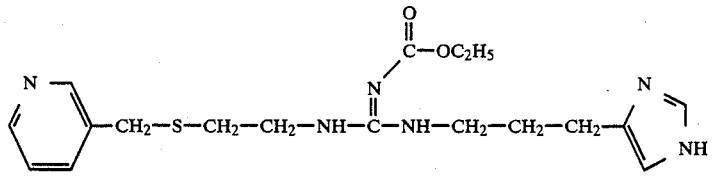

The method of preparation is analogous to that of Example 19, starting from 1.85 g (5 mmol) of N-{2-[(pyridin-3-yl)methylthio]ethyl}-S-methyl-isothiuronium iodide. Yield: 1.2 g (50%) of colourless crystals, m.p. 90° to 91° C. (ethyl acetate/ether).

$C_{18}H_{26}N_6O_2S$ (390.5) Analysis: calculated: C: 55.36; H: 6.71; N: 21.52; found: C: 55.38; H: 6.93; N: 21.45.

$^1$H-NMR data: (d$_6$-DMSO, TMS as internal standard) δ=1.15 (t) 3H 1.78 (m) 2H 2.5–2.65 (m) 4H 3.17 (m) 2H 3.38 (m) 2H 3.80 (s) 2H 3.93 (q) 2H 6.78 (broad) 1H 7.2 (very broad) 1H, replaceable by D$_2$O 7.34 (dd) 1H 7.53 (s) 1H 7.79 (d) 1H 8.45 (d) 1H 8.54 (s) 1H 7.95 (broad) 1H, replaceable by D$_2$O 11.85 (broad) 1H, replaceable by D$_2$O, ppm

EXAMPLE 22

N$^1$-ethoxycarbonyl-N$^2$-[3-(1H-imidazol-4-yl)propyl]-N$^3$-[2-(phenylmethylthio)ethyl]guanidine.

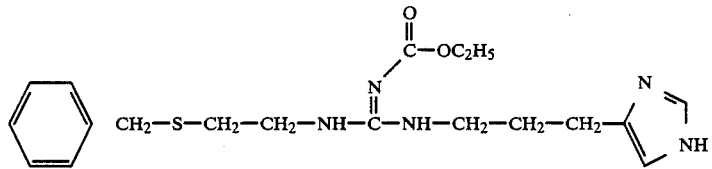

The method of preparation is analogous to that of Example 12, starting from 0.84 g (5 mmol) of 2-(phenylmethylthio)ethylamine. Yield: 1.0 g (51%) of colourless crystals, m.p. 91° to 92° C. (ethyl acetate/ether).

$C_{19}H_{27}N_5O_2S$ (389.5) Analysis: calculated: C: 58.59; H: 6.99; N: 17.98; found: C: 58.29; H: 7.00; N: 17.83.

MS (FAB method): m/z (rel. Int. [%])=390 ([M+H]$^+$, 23), 344 (11), 172 (9), 151 (10), 109 (47), 95 (11), 91 (100).

$^1$H-NMR data: (d$_6$-DMSO, TMS as internal standard) δ=1.15 (t) 3H 1.76 (m) 2H 2.5–2.65 (m, partially covered) 4H 3.18 (m) 2H 3.37 (m) 2H 3.76 (s) 2H 3.93 (q) 2H 6.77 (s) 1H 7.0 (broad) 1H, replaceable by D$_2$O 7.2–7.4 (m) 5H 7.53 (s) 1H 9.0 (broad) 1H, replaceable by D$_2$O 11.85 (broad) 1H, replaceable by D$_2$O, ppm

EXAMPLE 23

N$^1$-{2-[(2-diaminomethylene-aminothiazol-4-yl)methylthio]ethyl}-N$^2$-ethoxycarbonyl-N$^3$-[3-(1H-imidazol-4-yl)propyl]guanidine.

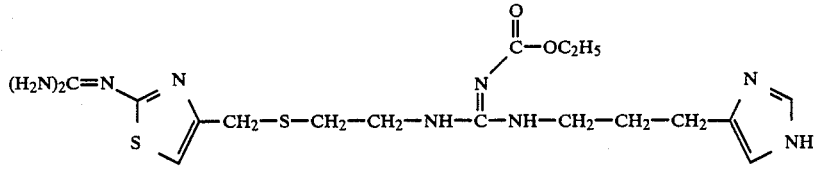

The method of preparation is analogous to that of Example 12, starting from 1.16 g (5 mmol) of 2-[(2-diaminomethylene-aminothiazol-4-yl)methylthio]ethylamine. Yield: 1.2 g (53%) of colourless crystals which sinter at 110° to 114° C. after recrystallization from ethyl acetate/ethanol.

$C_{17}H_{27}N_9O_2S_2$ (453.6) Analysis: calculated: C: 45.02; H: 6.00; N: 27.79; found: C: 44.79; H: 6.09; N: 28.07.

MS (FAB method): m/z (rel. Int. [%])=454 ([M+H]$^+$, 10), 408 (8), 211 (18), 155 (100), 113 (29), 109 (71), 95 (22), 93 (14), 82 (24), 81 (29).

$^1$H-NMR data: (d$_6$-DMSO, TMS as internal standard) δ=1.14 (t) 3H 1.77 (m) 2H 2.45–2.65 (m) 4H 3.18 (m) 2H 3.38 (m) 2H 3.61 (s) 2H 3.93 (q) 2H 6.56 (s) 1H 6.77 (s) 1H 6.84 (broad) 4H, replaceable by D$_2$O 7.75 (broad) 1H, replaceable by D$_2$O 7.52 (s) 1H 8.95 (broad) 1H, replaceable by D$_2$O 11.85 (broad) 1H, replaceable by D$_2$O, ppm

We claim:

1. A guanidine carboxylic acid ester corresponding to the formula

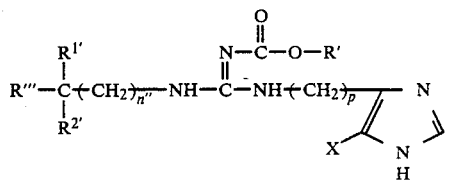

wherein one of R''' and R$^{2'}$ is pyridine and the other is hydrogen, unsubstituted or substituted phenyl or unsubstituted or substituted naphthyl, wherein the substitutions are selected from halogen atom, a straight chained $C_1$–$C_3$ alkyl group, and a straight chained $C_1$–$C_3$ alkoxy group, R$^{1'}$ is hydrogen or methyl, R' is a straight chained or branched $C_1$–$C_6$ alkyl group unsubstituted or substituted with at least one halogen atom, $C_1$–$C_3$ alkoxy group, phenyl group or naphthyl group, or R' is a cycloalkyl group having up to 6 carbon atoms or an unsubstituted or substituted phenyl ring wherein the substituents in the phenyl ring are selected from halogen atom, $C_1$–$C_3$ alkyl and $C_1$–$C_3$ alkoxy, X is a hydrogen atom or methyl group, p is 2 or 3, and n" is 2, 3, 4 or 5.

2. A guanidine carboxylic acid ester according to claim 1, wherein said ester is $N^1$-[3-(Imidazol-4-yl)propyl]-$N^2$-[4-(pyridin-2-yl)-butyl]-$N^3$-methoxycarbonylguanidine or a physiologically acceptable salt thereof.

3. A guanidine carboxylic acid ester according to claim 1, wherein said ester is $N^1$-[3-(Imidazol-4-yl)propyl]-$N^2$-[4-(pyridin-2-yl)butyl]-$N^3$-ethoxycarbonylguanidine or a physiologically acceptable salt thereof.

4. A guanidine carboxylic acid ester according to claim 1, wherein said ester is $N^1$-[3-(Imidazol-4-yl)propyl]-$N^2$-[3-(4-fluorophenyl)-3-(pyridin-2-yl)propyl]-$N^3$-methoxycarbonylguanidine or a physiologically acceptable salt thereof.

5. A guanidine carboxylic acid ester according to claim 1, wherein said ester is $N^1$-[3-(Imidazol-4-yl)propyl]-$N^2$-[3-(4-fluorophenyl)-3-(pyridin-2-yl)propyl]-$N^3$-ethoxycarbonylguanidine or a physiologically acceptable salt thereof.

6. A guanidine carboxylic acid ester according to claim 1, wherein said ester is $N^1$-[3-(Imidazol-4-yl)propyl]-$N^2$-[3-(4-fluorophenyl)-3-(pyridin-2-yl)propyl]-$N^3$-butoxycarbonylguanidine or a physiologically acceptable salt thereof.

7. A guanidine carboxylic acid ester according to claim 1, wherein said ester is $N^1$-[3-(Imidazol-4-yl)propyl]-$N^2$-[3-(4-fluorophenyl)-3-(pyridin-2-yl)propyl]-$N^3$-phenoxycarbonyl-guanidine.

8. A guanidine carboxylic acid ester according to claim 1, wherein said ester is $N^1$-[3-(Imidazol-4-yl)propyl]-$N^2$-[3-(4-fluorophenyl)-3-(pyridin-2-yl)propyl]-$N^3$-benzyloxycarbonyl-guanidine.

9. A guanidine carboxylic acid ester according to claim 1, wherein said ester is $N^1$-[3-(3,4-dichlorophenyl)-3-(pyridin-2-yl)propyl]-$N^2$-ethoxycarbonyl-$N^3$-[3-(1H-imidazol-4-yl)propyl]-guanidine.

10. A guanidine carboxylic acid ester according to claim 1, wherein said ester is $N^1$-[3-(3,4-difluorophenyl)-3-(pyridin-2-yl)propyl]-$N^2$-ethoxycarbonyl-$N^3$-[3-(1H-imidazol-4-yl)propyl]-guanidine.

11. A guanidine carboxylic acid ester according to claim 1, wherein said ester is $N^1$-[3-(3,5-difluorophenyl)-3-(pyridin-2-yl)propyl]-$N^2$-ethoxycarbonyl-$N^3$-[3-(1H-imidazol-4-yl)propyl]-guanidine.

12. A guanidine carboxylic acid ester according to claim 1, wherein said ester is $N^1$-[3-(4-fluorophenyl)-3-(pyridin-3-yl)propyl]-$N^2$-ethoxycarbonyl-$N^3$-[3-(1H-imidazol-4-yl)propyl]-guanidine.

13. A guanidine carboxylic acid ester according to claim 1, wherein said ester is $N^1$-[(1,1-dimethylethyl)oxycarbonyl]-$N^2$-[3-(4-fluorophenyl)-3-(pyridin-2-yl)propyl]-$N^3$-[3-(1H-imidazol-4-yl)propyl]-guanidine.

14. A guanidine carboxylic acid ester according to claim 1, wherein said ester is $N^1$-ethoxycarbonyl-$N^2$-[3-(1H-imidazol-4-yl)propyl]-$N^3$-[2-phenyl-2-(2-pyridyl)ethyl]-guanidine.

15. Pharmaceutical preparation having $H_2$-agonistic activity for treatment of heart disease, characterized in that it contains an effective amount of a compound according to claim 1 and at least one inert, pharmaceutically acceptable carrier or an inert, pharmaceutically acceptable diluent.

* * * * *